US010986842B2

(12) United States Patent
Bisgaard-Frantzen et al.

(10) Patent No.: US 10,986,842 B2
(45) Date of Patent: Apr. 27, 2021

(54) MICROBIAL PESTICIDAL COMPOSITION AND PRODUCTION THEREOF

(71) Applicant: CHR. HANSEN A/S, Hoersholm (DK)

(72) Inventors: Hans Bisgaard-Frantzen, Roedovre (DK); Michelle Madsen, Kirke Hyllinge (DK); Line Thorsen, Vanloese (DK); Jakob Worm, Vanloese (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

(21) Appl. No.: 15/774,430

(22) PCT Filed: Nov. 10, 2016

(86) PCT No.: PCT/EP2016/077347
§ 371 (c)(1),
(2) Date: May 8, 2018

(87) PCT Pub. No.: WO2017/081201
PCT Pub. Date: May 18, 2017

(65) Prior Publication Data
US 2018/0325118 A1 Nov. 15, 2018

(30) Foreign Application Priority Data

Nov. 10, 2015 (DK) .......................... PA 2015 00716
Jul. 22, 2016 (DK) .......................... PA 2016 00441
Jul. 22, 2016 (DK) .......................... PA 2016 00442

(51) Int. Cl.
| | | |
|---|---|---|
| *A01N 43/90* | (2006.01) | |
| *A01N 63/10* | (2020.01) | |
| *A01N 63/00* | (2020.01) | |
| *A01N 25/08* | (2006.01) | |
| *B01D 21/01* | (2006.01) | |
| *C07K 1/14* | (2006.01) | |
| *C12R 1/01* | (2006.01) | |

(52) U.S. Cl.
CPC ............. *A01N 63/10* (2020.01); *A01N 25/08* (2013.01); *A01N 43/90* (2013.01); *A01N 63/00* (2013.01); *B01D 21/01* (2013.01); *C07K 1/14* (2013.01); *C12R 1/01* (2013.01)

(58) Field of Classification Search
None
See application file for complete search history.

(56) References Cited

U.S. PATENT DOCUMENTS

| 5,470,827 A | 11/1995 | Tanaka et al. |
| 2011/0318386 A1 | 12/2011 | Jacobsen et al. |
| 2015/0147303 A1 | 5/2015 | Hsieh |

FOREIGN PATENT DOCUMENTS

| AU | 609631 B2 | 5/1991 |
| CA | 2238289 A1 | 11/1999 |
| CN | 103478146 A | 1/2014 |
| CN | 103788186 A | 5/2014 |
| CN | 10595543 A | 6/2016 |
| EP | 0013814 A1 | 8/1980 |
| EP | 2 311 936 | 4/2011 |
| EP | 2 796 044 | 10/2014 |
| ES | 2345969 A1 | 10/2010 |
| GB | 1 056 292 A | 1/1967 |
| RU | 2528058 C1 | 9/2014 |
| WO | WO-98/21968 | 5/1998 |
| WO | WO-98/50422 | 11/1998 |
| WO | WO-99/09819 | 3/1999 |
| WO | WO-00/29426 | 5/2000 |
| WO | WO-2013/110132 A1 | 8/2013 |
| WO | WO-2014/178032 A1 | 11/2014 |
| WO | WO-2015/024672 A1 | 2/2015 |

OTHER PUBLICATIONS

Gueldner, R. et al., J. Agric. Food Chem. 1988 vol. 36 pp. 366-370.*
Yeh, M.-S. et al., Biotechnol. Prog. 2005, vol. 21, pp. 1329-1334.*
Bais "Biocontrol of Bacillus subtilis against infection of *Arabidopsis* roots by Pseudomonas syringae is facilitated by biofilm formation and surfactin production," Plant Physiology, vol. 134, pp. 307-319, (Jan. 2004).
Brar et al., "Efficient centrifungal recovery of Bacillus thuringiensis biopesticides from fermented wastewater and wastewater sludge," Water Research, vol. 40, pp. 1310-1320 (2006).
Geuldner et al., "Isolation and Identification of Iturins as Antifungal Peptides in Biological Control of Peach Brown Rot with Bacillus Subtilis", Journal of Agricultural and Food Chemistry, (Mar. 1988) vol. 36, No. 2, pp. 366-370.
Johnprovis et al., "Geopolymer", Wikipedia, The Free Encyclopedia, (Mar. 25, 2016), URL: https://en.wikipedia.org/w/index.php?title=Geopolymer&oldid=711852559.
Ongena et al., "Bacillus lipopeptides: versatile weapons for plant disease biocontrol," Applied Microbiology and Biotechnology, vol. 16, No. 3, pp. 115-125, (2008).
Petrovic et al., "On the Particles Size Distributions of Diatomaceous Earth and Perlite Granulations", J Mechanical Engineering, vol. 57, pp. 843-850, (2011).
Shoda, "Bacterial Control of Plant Disease," Journal of Bioscience and Bioengineering, vol. 89, No. 6, pp. 515-521 (Mar. 2000).
Stein, "Bacillus subtilis antibiotics: structures, syntheses and specific functions," Molecular Microbiology, vol. 56, No. 4, pp. 854-857, (2005).
Yeh et al., "Enhanced Production of Surfactin from Bacillussubtilis by Addition of Solid Carriers", Biotechnology Progress, (Sep. 2005) vol. 21, No. 4, pp. 1329-1334.
McKeen et al., "Production and Partial Characterization of Antifungal Substances Antagonistic to *Monilinia fructicola* from *Bacillus subtilis*," Phytopathology, 76: 136-139 (1986).

* cited by examiner

*Primary Examiner* — Heidi Reese
(74) *Attorney, Agent, or Firm* — Foley & Lardner LLP (57) ABSTRACT

The present invention relates to a process for harvesting biomass of a bacterium, and/or a lipoprotein produced by a bacterium, which exhibit antifungal and antibacterial activity against various phytopathogenic agents.

13 Claims, 1 Drawing Sheet

MICROBIAL PESTICIDAL COMPOSITION AND PRODUCTION THEREOF

CROSS-REFERENCE TO RELATED APPLICATIONS

The present application is the U.S. National Stage of International Application PCT/EP2016/077347, filed Nov. 10, 2016, and claims priority to Danish Patent Application Nos. PA 2015 00716, filed Nov. 10, 2015, PA 2016 00441, filed Jul. 22, 2016, and PA 2016 00442, filed Jul. 22, 2016.

The present invention relates to a novel and improved process for harvesting biomass (including spores, bacteria cells) of a bacterium strain which exhibit antifungal and antibacterial activity against various phytopathogenic agents. In a specific embodiment, the invention provides a process for harvesting the biomass from a *Bacillus* culture medium involving acid treatment. The biomass obtained by the novel process exhibit surprisingly high antifungal activity due to content of lipopeptides.

BACKGROUND OF INVENTION

Among the microorganisms for biological control, bacteria of *Bacillus* sp. genus have received much attention due to the wide variety of antibiotic compounds they produce, their long shelf life, their fast growth in culture, and their ability to colonize leaf surfaces [1, 2, 3, 4]. In particular, certain species of *Bacillus* such as *Bacillus subtilis*, *Bacillus amyloliquefaciens*, *Bacillus cereus*, *Bacillus mycoides*, *Bacillus circulans*, *Bacillus megaterium*, *Bacillus pumilus*, *Bacillus mojavensis*, and *Bacillus thurigiensis* show antimicrobial activity.

The antimicrobial activity of these bacteria is due to their ability to produce lipopeptides e.g. of the surfactin, iturin, and fengycin families, which differ in the amino acid sequence and the branching of the fatty acid chain. Surfactins exhibit high antibacterial activity, whereas iturins and fengycins are recognized for their antifungal activity [4].

The prior art describes the use of *B. subtilis* and *B. amyloliquefaciens* to control various disease-causing microorganisms in a wide variety of crops, including fruit and vegetable crops such as blackberry, grape, raspberry, strawberry, tomato, cucumber, black pepper, orange, melon, apple, peach, custard apple, banana, papaya, mango, and kiwi. EP2311936 discloses a *B. subtilis* strain KS1 (NITE BP-569) as a biological control agent to counteract several phytopathogenic microorganisms in vine crops. WO 98/21968 discloses an antibiotic produced by *B. subtilis* AQ153 (ATCC 55614) effective against bacterial and fungal infections and also as method for protecting plants that comprises the application of these antibiotic compounds.

WO9850422, WO9909819, and WO0029426 disclose antibiotic compounds produced by the *B. subtilis* strain AQ713 (equivalent to strain QST713, deposited as NRRL B-21661) and its mutants which exhibit insecticidal, nematidical, antifungal, and antibacterial activity. US2011/0318386 describes methods for inducing systemic resistance against various pathogens through the use of biological controllers of the *Bacillus* genus, specifically of the isolated *B. mojavensis* 203-7 and isolated *B. mycoides* species. In turn, ES 2345969 describes a phytostrengthener for application on banana and plantain pseudostems, which includes *B. subtilis*, *Trichoderma viride*, and *B. megaterium* var phosphaticum.

WO14178032 discloses a process for increasing the production of biomass of microorganisms of the *Bacillus* genus, including *Bacillus subtilis* EA-CB0015 and *Bacillus amyloliquefaciens* EA-CB0959. The biomass obtained by the process can be separated from the culture medium using conventional methods of centrifugation or microfiltration, whereas the active metabolites can be obtained by extraction with solvents, precipitation, adsorption, or chromatography. In a preferred embodiment of the invention, the amount of biomass of microorganisms of *Bacillus* sp. obtained can range between 3.0 and 20.0 g/L.

The fungicidal activity of the isolated biomass (cells and spores) after harvesting from the culture medium is not satisfactory from a commercial view, and therefore the objection of the present invention is to provide an improved process for harvesting of biomass. The present inventors have revealed that amending the conditions during biomass harvest surprisingly increases the fungicidal activity of the harvested biomass.

U.S. Pat. No. 5,470,827 discloses that iturin A can be harvested from the culture medium by extraction with a solvent, or alternatively the culture medium may be filtered through a filter membrane or the like. If desired, the culture medium may be brought into contact with an active charcoal, powdery cellulose, adsorbing resin or the like carriers so that the produced iturin A is adsorbed to the carrier, and thereafter the product may be desorbed therefrom by elution.

The yields of the active metabolites are not satisfactory from a commercial view, and therefore an objection of the present invention is to provide an improved process for harvesting of the metabolites, especially lipoproteins and/or glycolipids.

SUMMARY OF INVENTION

It has surprisingly turned out that the improved biomass can be obtained by harvesting from a culture medium by a novel process which involves acid treatment. The biomass has unexpected higher antifungal activity that a comparative biomass obtained without acid treatment of the culture medium.

Thus, an aspect of the present invention relates to a process for harvesting of biomass from a bacteria (e.g. a *Bacillus*) culture medium (spent medium obtained by growth of a bacteria strain in a growth medium), the process comprises acidification of the culture medium, preferably after the bacteria culture has sporulated.

The harvested biomass is enriched with biosurfactants, especially a fengycin, and preferably contains a large number of colony forming units (viable cells and/or spores). In the most preferred embodiment, the process of the invention is carried out without use of any (organic) solvent or oil for extraction of biosurfactants.

If desired, the harvested biomass is dried and/or resuspended in an agricultural acceptable liquid.

Also, the present inventors have surprisingly found out that the metabolites can be harvested from a culture medium by adsorption on e.g. diatomaceous earth (aka kieselguhr). It is contemplated that other geopolymers (natural occurring or synthetic made) or similar materials are applicable as adsorbent. The term geopolymer should in the present context be understood broadly, and encompasses biominerals and geominerals, etc.

Thus, an aspect of the present invention relates to a process for harvesting of metabolites (esp. lipopeptides or glycolipids) from a bacteria (e.g. a *Bacillus*) culture supernatant or culture medium (obtained by growth/propagation of a bacteria strain in a growth medium), optionally the supernatant is separated from the biomass by centrifugation and/or filtration), the process comprises addition of a geopolymer, e.g. kieselguhr, preferably in an amount corresponding to a loading capacity. The lipopeptide/glucolipid (of e.g. surfactin, iturin and fengycin families) concentration in the spent culture medium (or supernatant) varies depending of the strain used for fermentation. The skilled person knows how to optimize the amount of geopolymer, e.g. kieselguhr, to be added, for instance he can calculate the amount of lipopeptide/glucolipid to be adsorbed by means of HPLC analysis of the medium/supernatant. The loading capacity for kieselguhr is expected to be 0.02 g-0.3 g kieselguhr per ml culture medium (or culture supernatant).

The mixture of supernatant or culture medium with geopolymer, e.g. kieselguhr, material is preferably incubated at room temperature, and/or for ½-3 h (hours) and/or @ 25 rpm and/or at an appropriate pH ranging from pH 4-10. Preferably the pH is adjusted after end fermentation, but pH can also be adjusted during fermentation.

After end incubation, geopolymer, e.g. kieselguhr, and any remaining biomass is isolated using centrifugation and/or filtration, such as dead end filtration.

If desired, the product resulting from the centrifugation and/or filtration (containing the geopolymer, e.g. kieselguhr, with adsorbed lipoprotein/glycolipid and optionally biomass) is resuspended in an agricultural acceptable liquid.

Alternatively—when filtration is used—all or a portion of the geopolymer, e.g. kieselguhr, can be added as filter aid, so that it can adsorb the metabolites during the filtration step.

The bacterial strain to be used in a process of the present invention should be able to produce antifungal metabolites in commercially relevant amounts, examples on suitable strains are: *Bacillus amyloliquefaciens* strains HSCC 124 (FERM BP-4758) or IAM 1523 (cf. U.S. Pat. No. 5,470,827); *Bacillus subtilis* strain KS1 (NITE BP-569) (cf. EP2311936) and *Bacillus subtilis* strain AQ153 (ATCC55614) (cf. WO9821968). Other relevant strains are known from the literature, e.g. the literature mentioned in the present specification.

DETAILED DISCLOSURE

In a first aspect, the present invention relates to a process for harvesting biomass (bacteria cells and/or spores) from a culture medium, the process involves lowering the pH of the medium, e.g. to a pH below 6.0.

Presently preferred embodiments of this first aspect are:

Embodiment A

A process for harvesting biomass (bacteria cells and/or spores) with fungicidal activity by
a) obtaining a culture medium by propagating a lipoprotein and/or a glycolipid producing bacteria strain in a growth medium at a pH in the range 6.5 to 10.0;
b) lowering the pH of the culture medium to below 6.5 (such as below 6.4, or in the range 2.1 to 6.4, in the range 2.5 to 5.9, in the range 3.0 to 5.4, in the range 3.0 to 5.0, in the range 3.0 to 4.5, or in the range 3.5 to 4.5), e.g. by addition of an acid;
c) optionally adding a geopolymer, either before, during or after step b); and
d) separating the biomass from the culture medium, e.g. by centrifugation of filtration.

Embodiment B

A process for harvesting biomass (bacteria cells and/or spores) with fungicidal activity by
a) obtaining a culture medium by propagating a lipoprotein and/or a glycolipid producing bacteria strain in a growth medium at a pH in the range 6.0 to 9.0;
b) lowering the pH of the culture medium to below 6.0 (such as below 5.9, or in the range 2.1 to 5.9, in the range 2.5 to 5.9, in the range 3.0 to 5.0, in the range 3.0 to 4.5, or in the range 3.5 to 4.5), e.g. by addition of an acid;
c) optionally adding a geopolymer, either before, during or after step b); and
d) separating the biomass from the culture medium, e.g. by centrifugation of filtration.

Embodiment C

A process for harvesting biomass (bacteria cells and/or spores) with fungicidal activity by
a) obtaining a culture medium by propagating a lipoprotein and/or a glycolipid producing bacteria strain in a growth medium at a pH in the range 5.5 to 9.0;
b) lowering the pH of the culture medium to below 5.5 (such as below 5.4, or in the range 2.1 to 5.4, in the range 2.5 to 5.4, in the range 3.0 to 5.0, in the range 3.0 to 4.5, or in the range 3.5 to 4.5), e.g. by addition of an acid;
c) optionally adding a geopolymer, either before, during or after step b); and
d) separating the biomass from the culture medium, e.g. by centrifugation of filtration.

Embodiment D

A process for harvesting biomass (bacteria cells and/or spores) with fungicidal activity by
a) obtaining a culture medium by propagating a lipoprotein and/or a glycolipid producing bacteria strain in a growth medium at a pH in the range 5.6 to 7.4;
b) lowering the pH of the culture medium to below 5.5 (such as below 5.4, or in the range 2.1 to 5.5, in the range 2.5 to 5.4, in the range 3.0 to 5.0, in the range 3.0 to 4.5, or in the range 3.5 to 4.5), e.g. by addition of an acid;
c) optionally adding a geopolymer, either before, during or after step b); and
d) separating the biomass from the culture medium, e.g. by centrifugation of filtration.

Embodiment E

A process for harvesting biomass (bacteria cells and/or spores) with fungicidal activity by
a) obtaining a culture medium by propagating a lipoprotein and/or a glycolipid producing bacteria strain in a growth medium at a pH in the range 5.7 to 9.0;
b) securing that the pH of the culture medium is in range 2.5 to 5.5 (such as in the range 3.0 to 5.0, in the range 3.0 to 4.5, or in the range 3.5 to 4.5), e.g. by addition of an acid;
c) optionally adding a geopolymer, either before, during or after step b); and
d) separating the biomass from the culture medium, e.g. by centrifugation of filtration.

Embodiment F

A process for harvesting biomass (bacteria cells and/or spores) with fungicidal activity by
  a) obtaining a culture medium by propagating a lipoprotein and/or a glycolipid producing bacteria strain in a growth medium;
  b) securing that the pH of the culture medium is in range 2.5 to 5.5 (such as in the range 3.0 to 5.0, in the range 3.0 to 4.7, or in the range 3.5 to 4.5), e.g. by addition of an acid (by securing is understood lowering the pH the specified value, if necessary);
  c) optionally adding a geopolymer, either before, during or after step b);
  d) separating the biomass from the culture medium, e.g. by centrifugation of filtration;
  e) optionally adding an excipient (such as a carrier or a protectant) to the biomass; and/or optionally adjusting the pH to a pH in the range 5.5 to 8.0; and
  f) optionally drying, e.g. spray drying, freeze drying or vacuum drying, the biomass.

Embodiment G

A process for harvesting biomass (bacteria cells and/or spores) with fungicidal activity by
  a) providing a culture medium obtained by propagating a lipoprotein and/or a glycolipid producing bacteria strain in a growth medium, said medium having a pH above 5.7;
  b) lowering the pH of the culture medium to a pH in range 2.5 to 5.5 (such as in the range 3.0 to 5.0, in the range 3.0 to 4.7, or in the range 3.5 to 4.5), e.g. by addition of an acid;
  c) optionally adding a geopolymer, either before, during or after step b)
  d) separating the biomass from the culture medium, e.g. by centrifugation of filtration;
  e) optionally adding an excipient (such as a carrier or a protectant) to the biomass; and/or optionally adjusting the pH to a pH in the range 5.5 to 8.0; and
  f) optionally drying, e.g. spray drying, freeze drying or vacuum drying, the biomass.

Embodiment H

A process for obtaining biomass (bacteria cells and/or spores) with fungicidal activity by
  a) providing a culture medium obtained by propagating a lipoprotein and/or a glycolipid producing bacteria strain in a growth medium, said medium having a pH in the range 2.5 to 6.5 (such as in the range 4.0 to 6.0, in the range 4.5 to 6.0, in the range 3.0 to 5.0, in the range 3.0 to 4.7, or in the range 3.5 to 4.5);
  b) optionally adding a geopolymer, either before, during or after step b)
  c) separating the biomass from the culture medium, e.g. by centrifugation of filtration;
  d) optionally adding an excipient (such as a carrier or a protectant) to the biomass; and/or optionally adjusting the pH to a pH in the range 5.5 to 8.0; and
  e) optionally drying, e.g. spray drying, freeze drying or vacuum drying, the biomass.

More preferred embodiments of any of the above processes (embodiments A to H) according to the invention are:
  A process where the pH of the culture medium in a) is above 5.7, such as in the range 5.7 to 9, in the range 6.0 to 9.0, or in the range 6.5 to 8. It is presently preferred that the pH is kept within the specified range for at least 1 hour, such as at least 2 hours, at least 4 hours, at least 10 hours or at least 24 hours.
  A process wherein the culture medium in a) comprises at least 5 g biomass per liter culture medium, such as at least 7 g/L or at least 10 g/L.
  A process wherein the culture medium in a) comprises at least 200 mg metabolites per liter culture medium, such as at least 400 mg/L or at least 600 mg/L.
  A process for harvesting biomass (bacteria cells and/or spores) with fungicidal activity by
    a) obtaining a culture medium which contains at least 5 g/L biomass of *Bacillus* bacteria, and at least 200 mg/L metabolites of the surfactin, iturin, plipastatin, arthrofactin, serrawettin, or fengycin families, preferably having a pH in the range 5.6 to 7.4;
    b) lowering (if necessary) the pH of the culture medium to below 5.5 (such as below 5.4, or in the range 2.1 to 5.5, in the range 2.5 to 5.4, in the range 3.0 to 5.0, in the range 3.0 to 4.5, or in the range 3.5 to 4.5), e.g. by addition of an acid;
    c) optionally adding a geopolymer, either before, during or after step b); and
    d) separating the biomass from the culture medium, e.g. by centrifugation of filtration.
  A process where the pH in step b) is below 5.7, such as in the range 2.0 to 5.6, in the range 3.0 to 5.5, in the range 3.5 to 5.5, in the range 4.0 to 5.3, in the range 4.0 to 5.0, or in the range 4.5 to 5.0. It is presently preferred that the pH value is kept within the specified range for at least 10 minutes, such as at least 20 minutes, at least 30 minutes, or at least 60 minutes.
  A process where the pH in step b) is in the range 4.0 to 5.0, or in the range 4.5 to 5.0. It is presently preferred that the pH value is kept within the specified range for at least 10 minutes, such as at least 20 minutes, at least 30 minutes, or at least 60 minutes.
  A process wherein the geopolymer is selected from the group consisting of: diatomite, kieselguhr, kaolin, chinese clay, bentonite, talcum, volcanic ash, volcanic rock, clay, lignin, drilling mud, diatomaceous earth, synthetic silica, surface-treated diatomaceous earth, and metal silicate. Interesting geopolymer is diatomaceous earth or surface-treated diatomaceous earth. Preferably, the geopolymer is used in an amount of 0.02 g to 0.3 g per ml liquid suspension or solution of lipoprotein and/or glycolipid
  A process wherein the bacterial strain belongs to a *Bacillus* species, such as *Bacillus subtilis* or *Bacillus amyloliquefaciens*, such as a strain selected from the group consisting of *Bacillus amyloliquefaciens* strains HSCC 124 (FERM BP-4758) or IAM 1523, *Bacillus subtilis* strains KS1 (NITE BP-569) and AQ153 (ATCC55614). Interesting bacterial strains is a strain selected from the group consisting of *Bacillus amyloliquefaciens* strains HSCC 124 (FERM BP-4758) or IAM 1523, *Bacillus subtilis* strains KS1 (NITE BP-569) and AQ153 (ATCC55614).
  A process wherein the lipoprotein and/or the glycolipid is selected from the group consisting of surfactin, iturin, plipastatin, arthrofactin, serrawettin, and fengycin or derivates of any of these.

In a second aspect, the present invention relates to a process for harvesting a lipoprotein and/or a glycolipid from a liquid suspension or solution (said suspension or solution contains the lipoprotein or glycolipid) by a method comprising
   a) contacting a geopolymer with the liquid suspension or solution; and
   b) allowing the geopolymer to adsorb (or bind) the lipoprotein or glycolipid; and
   c) separating the geopolymer from the liquid; and
   d) optionally separating the lipoprotein or glycolipid from the geopolymer, e.g. desorbing the lipoprotein and/or glycolipid.

An embodiment of the second aspect relates to a process for harvesting a lipoprotein and/or a glycolipid from a liquid (said liquid contains the lipoprotein or glycolipid) by a method comprising
   a) contacting a geopolymer with the liquid; and
   b) allowing the geopolymer to adsorb (or bind) the lipoprotein or glycolipid; and
   c) separating the geopolymer from the liquid; and
   d) optionally separating the lipoprotein or glycolipid from the geopolymer, e.g. desorbing the lipoprotein and/or glycolipid.

In an interesting embodiment of the second aspect relates to the process wherein the liquid suspension or solution is obtained by:
   i) growing a bacterium strain (which is able to produce the lipoprotein and/or the glycolipid) in a suitable liquid growth medium, thereby obtaining a liquid suspension or solution of lipoprotein and/or the glycolipid; and
   ii) optionally removing bacteria cells from the suspension or solution; and
   iii) optionally disrupting the bacteria cells.

Another interesting embodiment of the second aspect is a process for preparing a dry composition comprising a lipoprotein and/or a glycolipid, by a method comprising
   i) growing a bacterium strain (which is able to produce the lipoprotein and/or the glycolipid) in a suitable liquid growth medium, thereby obtaining a liquid suspension or solution of lipoprotein and/or the glycolipid; and
   ii) optionally removing bacteria cells from the suspension or solution; and
   ii) optionally disrupting the bacteria cells; and
   a) contacting a geopolymer with the suspension or solution; and
   b) allowing the geopolymer to adsorb the lipoprotein or glycolipid; and
   c) separating the geopolymer from the liquid suspension or solution; and
   d) optionally separating the lipoprotein and/or glycolipid from the geopolymer, e.g. desorbing the lipoprotein and/or glycolipid; and
   e) optionally adding an excipient (such as a carrier or a protectant) to the lipoprotein/glycolipid containing fraction; and
   f) drying, e.g. spray drying, freeze drying or vacuum drying, the lipoprotein and/or glycolipid containing fraction.

As adsorbent is presently preferred a geopolymer selected from the group consisting of: a biomineral, a geomineral, diatomite, kieselguhr, kaolin, chinese clay, bentonite, talcum, volcanic ash, volcanic rock, clay, lignin, drilling mud, diatomaceous earth, surface-treated diatomaceous earth, synthetic silica, and metal silicate. Presently preferred adsorbents are biominerals. Presently most preferred geopolymer is diatomaceous earth (e.g. surface-treated or activated, e.g. by heat treatment).

The geopolymer is normally used in an amount of 0.02 g to 0.3 g per ml liquid suspension or solution of lipoprotein and/or glycolipid, but it is contemplated that other amounts can be used, e.g. from 0.005 to 0.02 g/ml, or higher than 0.3 g/ml, depending on the amount of metabolite in the solution or suspension, and on the geopolymer. It is presently preferred to use a biomineral as adsorbent, and more preferably diatomaceous earth. If biomineral is used, the presently preferred amount is in the range 0.02-0.2 g/ml, or more preferably in the range 0.04 to 0.1 g/ml.

The process steps a, b, c and d can be performed at a temperature in the range 0 to 50° C., such as in the ranges 5 to 30° C. or 15 to 25° C., but it is presently preferred that the process is performed at ambient temperature (around 20° C.). In order to speed up the process, the step allowing the geopolymer to adsorb the lipoprotein or glycolipid (i.e. the incubation step) preferably includes stirring of the liquid, e.g. at 25 rpm or faster. The pH can be optimized by the skilled person, it is presently preferred that the pH of the liquid is adjusted before or during the contact with the geopolymer, such as to a pH in the range 4 to 10.

Other interesting embodiments of the second aspect are:
   A process wherein the adsorption step b) is carried out at a pH in the range 3 to 10, such as in the range 3.5 to 7, or preferably in the range 4 to 5.5.
   A process wherein adsorption step b) is carried out at a temperature in the range 0 to 50° C., such as in the range 5 to 40° C. or preferably in the range 10 to 30° C.
   A process wherein adsorption step b) is carried out for a time period in the range 0.1 to 24 h, such as in the range 0.5 to 10 h, or preferably in the range 1 to 4 h.
   A process wherein step d), if present, is carried out at a pH in the range 3 to 10, such as in the range 3.5 to 7, or preferably in the range 4 to 5.5.
   A process wherein step d), if present, is carried out at a temperature in the range 0 to 50° C., such as in the range 5 to 40° C. or preferably in the range 10 to 30° C.
   A process wherein step d) is carried out for a time period in the range 0.1 to 24 h, such as in the range 0.5 to 10 h or preferably in the range 1 to 4 h.
   A process wherein the geopolymer is a biomineral, such as kieselguhr.
   A process wherein the geopolymer is a geomineral, such as perlite.
   A process wherein the geopolymer is in powder form.
   A process where the lipoprotein and/or a glycolipid is a lipopeptide.
   A process where the lipoprotein and/or a glycolipid is a surfactin.
   A process where the lipoprotein and/or a glycolipid is an iturin.
   A process where the lipoprotein and/or a glycolipid is a fengycin.
   A process where the lipoprotein and/or a glycolipid is a mixture comprising lipopeptides of the surfactin, iturin, and fengycin families The process can be used for harvesting lipopeptides/glycolipids from any liquid, but it is preferred that liquid is a fermentate or supernatant obtained by fermenting a growth medium with a microorganism, such as a strain of a bacterium. It is presently preferred that the bacterial strain belongs to a *Bacillus* species, such as *Bacillus subtilis* or *Bacillus amyloliquefaciens*. Examples on strains are strains selected from the group consisting of *Bacillus amyloliquefaciens* strains HSCC 124 (FERM BP-4758) or IAM 1523, or *Bacillus subtilis* strains KS1 (NITE BP-569) or AQ153 (ATCC55614). An interesting strain is QST713 (NRRL B-21661).

In a specific embodiment of the process, the lipoprotein and/or the glycolipid is selected from the group consisting of surfactin, iturin, plipastatin, arthrofactin, serrawettin, gageotetrin (A, B or C), gageostatin (A, B or C), and fengycin or derivates of any of these. Presently most interesting lipoproteins are of the surfactin, iturin, and fengycin families. If the lipoprotein and/or the glycolipid is found intracellularly, the cells can be disrupted, e.g. mechanically, ultrasonically, chemically or enzymatically.

The second aspect comprises the following embodiments:

Embodiment 1

A process for harvesting a lipopeptide of the surfactin, iturin, and fengycin families from a liquid suspension or solution by a method comprising
a) contacting a biomineral (such as diatomaceous earth) with the liquid suspension or solution, such as a *Bacillus* culture medium; and
b) allowing the biomineal to adsorb (or bind) the lipopeptide; and
c) separating the biomineral from the liquid; and
d) optionally separating the lipopeptide from the biomineral, e.g. desorbing the lipopeptide.

In this process the adsorption step b) is preferably carried out at a pH in the range 3 to 10, such as in the range 3.5 to 7, in the range 4 to 7, in the range 5 to 8, or in the range 4 to 5.5. It is presently most preferred to adsorb at the pH of the culture medium, which normally is in the range 5.5 to 7.

Embodiment 2

A process for harvesting a lipopeptide of the surfactin, iturin, and fengycin families from a liquid suspension or solution by a method comprising
a) contacting a geomineral (such as perlite) with the liquid suspension or solution, such as a *Bacillus* culture medium; and
b) allowing the geomineal to adsorb (or bind) the lipopeptide; and
c) separating the geomineral from the liquid; and
d) optionally separating the lipopeptide from the geomineral, e.g. desorbing the lipopeptide.

In this process the adsorption step b) is preferably carried out at a pH in the range 3 to 10, such as in the range 3.5 to 7, in the range 4 to 7, in the range 5 to 7, or in the range 4 to 5.5. It is presently most preferred to adsorb at the pH of the culture medium, which normally is in the range 5.5 to 7.

It should be understood that the first and second aspect of the invention can be combined, e.g. the process of the second aspect may be performed on any suspension or solution arising during the process of the first aspect, such as the supernatant after harvesting of the biomass/spore material.

A third aspect of the present invention relates to a composition obtainable by a process of the second aspect of the invention. Such a composition might substantially consist of a geopolymer in combination with a lipoprotein and/or glycolipid.

An interesting embodiment is a composition comprising a geopolymer; and a lipoprotein and/or glycolipid, wherein at least 10%, such as at least 30% or at least 50% (w/w) of the lipoprotein and/or glycolipid is adsorbed (or bound) to the surface of the geopolymer. Especially interesting compositions according to the above aspect are:

A composition wherein the geopolymer is a biomineral, such as kieselguhr.

A composition wherein the geopolymer is a geomineral, such as perlite.

A composition wherein the geopolymer is in powder form.

A composition where the lipoprotein and/or a glycolipid is a lipopeptide.

A composition where the lipoprotein and/or a glycolipid is a surfactin.

A composition where the lipoprotein and/or a glycolipid is an iturin.

A composition where the lipoprotein and/or a glycolipid is a fengycin.

A composition where the lipoprotein and/or a glycolipid is a mixture comprising lipopeptides of the surfactin, iturin, and fengycin families.

If a pH range is specified according to a process of this invention, it is presently preferred that the pH value is kept within the specified range for at least 10 minutes, such as at least 20 minutes, at least 30 minutes, or at least 60 minutes.

A fourth aspect of the present invention relates to the use of a geopolymer as adsorbent for a lipoprotein or a glycolipid, or the use of a geopolymer for harvesting of a lipoprotein or a glycolipid from a culture medium.

A fifth aspect of the present invention relates to the use of a geopolymer as and aid for harvesting biomass, e.g. in a process for harvesting spores after acid adjustment of the culture medium.

Interesting embodiments of any use aspects are:
A use wherein the geopolymer is a biomineral, such as kieselguhr.

A use wherein the geopolymer is a geomineral, such as perlite.

A use wherein the geopolymer is in powder form.

A use wherein the medium contains a lipoprotein and/or glycolipid.

A use where the lipoprotein and/or a glycolipid is a lipopeptide.

A use where the lipoprotein and/or a glycolipid is a surfactin.

A use where the lipoprotein and/or a glycolipid is an iturin.

A use where the lipoprotein and/or a glycolipid is a fengycin.

A use where the lipoprotein and/or a glycolipid is a mixture comprising lipopeptides of the surfactin, iturin, and fengycin families A sixth aspect of the present invention relates to a composition obtainable by a process of the first aspect of the invention, such a composition comprising *Bacillus subtilis* spores, a composition comprising *Bacillus amyloliquefaciens* spores, and/or a geopolymer and *Bacillus* spores. The composition might be applied to the plants as a liquid suspension, or as a powder. The compositions of the invention might comprise an excipient such as a geopolymer.

Definitions

In the present context, the term geopolymer includes geominerals, biominerals, minerals of geological or biological origin, sedimentary rock material (e.g. powder) and silicon based polymers. Examples on geopolymers are given in WO2015024672A1. Presently preferred geopolymers are kieselguhr, diatomite, diatomaceous earth, Kaolin (Chinese clay), bentonite, talcum, volcanic ash, volcanic rock, clay, perlite, lignin, drilling mud, diatomic earth, synthetic silica's, etc., said material optionally being modified, e.g. treated with chemicals or heat. The term both covers dried material and wet material. The geopolymer is preferable used as a powder. If needed, the geopolymer can be grinded to obtain particles (or a powder). The size of the geopolymer particles can vary depending on the geopolymer and/or the selected method for separation of the particles from the spent culture medium or supernatant and/or the intended use of the resulting product. It is presently preferred that the particle size is in the range 3 micrometres to more than 1 millimetre, more preferred 10 to 200 micrometres.

In the present context, the term lipoprotein includes lipopeptides. The terms may be used interchangeably with biosurfactant. The lipopeptide may originate from a lipopeptide-producing strain of e.g. *Bacillus subtilis* or *Bacillus amyloliquefaciens*. It may be an iturin-type compound, a surfactin-type compound, a fengycin-type compound, or a combination thereof. In one embodiment, the lipopeptide is a combination of an iturin-type compound, a surfactin-type compound, and a fengycin-type compound. In other embodiments, the lipopeptide is a combination of an iturin-type compound and a surfactin-type compound; a combination of an iturin-type compound and a fengycin-type compound; or a combination of a surfactin-type compound and a fengycin-type compound. In some embodiments, the total concentration of the lipopeptide described above is at least 1 mg/g, at least 2 mg/g, at least 3 mg/g, at least 4 mg/g, at least 5 mg/g, at least 6 mg/g, at least 7 mg/g, at least 8 mg/g, at least 9 mg/g, at least 10 mg/g, at least 11 mg/g, at least 12 mg/g, at least 13 mg/g, at least 14 mg/g, or at least 15 mg/g in the biomass of the strain of e.g. *Bacillus subtilis* or *Bacillus amyloliquefaciens*.

In one embodiment, the lipopeptide is an iturin-type compound. The iturin-type compound may be bacillomycin D, bacillomycin F, bacillomycin L, bacillomycin LC (bacillopeptin), mycosubtilin, iturin A, iturin AL, or iturin C. In another embodiment, the lipopeptide is a fengycin-type compound. The fengycin-type compound may be fengycin A, fengycin B, plipastatin A, plipastatin B, or an agrastatin. In yet another embodiment, the lipopeptide is a surfactin-type compound. The surfactin-type compound may be esperin, lichenysin, pumilacidin, or surfactin.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXAMPLES

Example 1: Obtaining Biomass of *Bacillus subtilis* and *Bacillus amyloliquefaciens*

The *Bacillus* strains were grown essential as disclosed in [6]. More specifically, a *Bacillus subtilis* strain was inoculated in a typical growth medium (comprising, in w/v percentages, 4% glucose, 4% yeast extract, 0.004% manganese sulfate, 0.003% calcium chloride, 0.1% ammonium sulfate, 0.4% magnesium sulfate, 0.05% disodium phosphate and 0.05% dipotassium phosphate). Fermentation was carried out in 500 mL flasks with 100 mL of medium at a temperature of 30 degrees centigrade and 200 rpm in an orbital shaker. Each Erlenmeyer was inoculated with 10 mL of a bacterial suspension. The *B. subtilis* culture was fermented at pH 7.5.

Example 2. Harvesting High Active Biomass from *Bacillus* Strain

After end fermentation pH of the culture medium obtained in example 1 was adjusted from pH 7.5 down to pH 5.5. The culture medium was agitated gentle (approx. 50 rpm) at room temperature for 1 hr. After end agitation the biomass was isolated by filtration. The isolated biomass was collected in an appropriate beaker and the pH adjusted to pH 7.2. The pH adjusted biomass was gentle agitated for 1 hr. at 50 rpm before freeze dried.

Example 3. Harvesting High Active Biomass from *Bacillus* Strain

After end fermentation pH of the culture medium obtained in example 1 was adjusted from pH 7.5 down to pH 4.5. The culture medium was agitated gentle (approx. 50 rpm) at room temperature for 1 hr. After end agitation the biomass was isolated by filtration. The isolated biomass was collected in an appropriate beaker and the pH adjusted to 7.2. The pH adjusted biomass was gentle agitated for 1 hr at 50 rpm before freeze dried.

Example 4. Harvesting High Active Biomass from *Bacillus* Strain

After end fermentation (EoF) the pH of the culture medium obtained in example 1 is adjusted from pH 7.5 down to pH 4.5. Diatomic earth is added. The culture medium is agitated gentle at room temperature for 1 hr. After end agitation the biomass was isolated by filtration. The isolated biomass is collected in an appropriate beaker and the pH is adjusted to 7.2. The pH adjusted biomass is agitated for 1 hr at 50 rpm and freeze dried.

Example 5. Harvesting High Active Biomass from *Bacillus* Strain Culture Medium

Three samples of the culture medium obtained in example 1 were adjusted to the following pH values: 6.0, 5.0 and 4.5, respectively. A fourth sample of the culture medium (pH 7.5) was used as control. The samples were agitated gentle (approx. 50 rpm) at room temperature. After end agitation the biomass of the samples was isolated by filtration. The isolated biomass was collected in appropriate beakers and the pH adjusted to 7.2 and the content of antifungal metabolites (fengycin, iturin and surfactin) was measured by HPLC and MS. See table 1 below.

TABLE 1

| pH | % recovery of metabolites in biomass fraction 2 h |
|---|---|
| 4.5 | 98% |
| 5.0 | 98% |
| 6.0 | 90% |
| 7.5 (control) | 69% |

Example 6. Adsorption of Fengycin, Iturin and Surfactin to Solid Support of Geo and Bio Minerals Origin—Harvesting Active Metabolites of *Bacillus* Strains The *B. subtilis* culture medium obtained according to Example 1, was after end fermentation divided in 3 fractions and adjusted to pH 5, pH 7 and pH 8.7 respectively. 3.5 g geopolymer (geomineral or bio mineral) was mixed with 45 ml culture medium adjusted to the different pH values (0.08 g geo or bio mineral per ml spent culture medium I). The medium with geo or bio mineral was incubated at room temperature for 3 hrs. @ 25 rpm. After end of incubation, geo or bio mineral solutions were isolated together with the biomass by centrifugation. Samples for lipopeptides analysis were taken from, pH adjusted culture medium before incubation and supernatant isolated using centrifugation after incubation. % lipopeptides adsorbed to the geo/bio mineral was calculated from the differences in lipopeptide concentrations.

The geo/bio minerals material tested included:
1. Reference—only spores (biomass).
2. Harborlite 300 (Perlite/Volcanic rock).
3. Harborlite 635 (Perlite/Volcanic rock).
4. Harborlite 900 (Perlite/Volcanic rock).
5. Europerl (Perlite/Volcanic rock).
6. Hyflo Supercel (Celite/Diatomic Earth).
7. Celite 545 (Celite/Diatomic Earth).
8. Filtercel (Diatomic Earth).
9. Kaoline Supreme (Chinese clay).
10. Kaoline Optigloss (Chinese clay).
11. Sipernat 50 S-Silica (Synthetic silica Aerosil/Evonike).
12. Aerosil 380 F-Silica (Synthetic silica Aerosil/Evonike).

Samples collected were stored at −20° C./−50° C. until further analysis of the lipopeptide content by HPLC and MS. Results for adsorption of metabolites Fengycin, Iturin and Surfactin to the different geo/bio minerals are summarized in the below table 2:

TABLE 2

| Adsorption material | Lipo component | % Adsorption pH 5 | pH 7 | pH 8.7 |
|---|---|---|---|---|
| FM - reference/Spores | % Fengycin | 96% | 94% | 88% |
| | % Iturin | 96% | 81% | 60% |
| | % Surfactin | 95% | 93% | 92% |
| FM + Harborlite 300/ Perlite - Volcanic rock | % Fengycin | 99% | 97% | 92% |
| | % Iturin | 96% | 97% | 94% |
| | % Surfactin | 95% | 94% | 92% |
| FM + Harborlite 635/ Perlite - Volcanic rock | % Fengycin | 100% | 99% | 97% |
| | % Iturin | 96% | 97% | 95% |
| | % Surfactin | 99% | 98% | 97% |
| FM + Harborlite 900/ Perlite - Volcanic rock | % Fengycin | 100% | 98% | 95% |
| | % Iturin | 96% | 96% | 93% |
| | % Surfactin | 99% | 97% | 97% |
| FM + Hyflo Supercel/ Diatomic earth | % Fengycin | 99% | 99% | 100% |
| | % Iturin | 96% | 97% | 98% |
| | % Surfactin | 96% | 95% | 96% |
| Fm + Celite 545/ Diatomic earth | % Fengycin | 99% | 99% | 99% |
| | % Iturin | 97% | 97% | 97% |
| | % Surfactin | 95% | 95% | 95% |
| FM + Filtercel/ Diatomic earth | % Fengycin | 100% | 98% | 95% |
| | % Iturin | 96% | 96% | 93% |
| | % Surfactin | 99% | 97% | 97% |
| FM + Kaoline Supreme | % Fengycin | 100% | 100% | 99% |
| | % Iturin | 97% | 97% | 96% |
| | % Surfactin | 99% | 98% | 98% |
| FM + SIPERNAT 50 S-Silica (Synthetic silica Aerosil/Evonike) | % Fengycin | 100% | 100% | 100% |
| | % Iturin | 97% | 96% | 97% |
| | % Surfactin | 99% | 98% | 99% |
| FM + Aerosil 380 F-Silica (Synthetic silica Aerosil/Evonike) (1.5 g/45 g FM) | % Fengycin | 100% | 100% | 99% |
| | % Iturin | 97% | 97% | 95% |
| | % Surfactin | 99% | 99% | 98% |
| FM + Europerl Perlite - Volcanic rock | % Fengycin | 99% | 98% | 93% |
| | % Iturin | 95% | 95% | 93% |
| | % Surfactin | 99% | 97% | 94% |
| FM + Kaoline - Optigloss | % Fengycin | 100% | 99% | 97% |
| | % Iturin | 96% | 96% | 92% |
| | % Surfactin | 99% | 98% | 96% |

The pH adjusted culture medium use as starting material for the batch adsorption experiments consisted of lipopeptides with a concentration on approx. 421 µg/ml (microgram/ml) for Fengycin, 357 µg/ml Iturin and 1141 µg/ml Surfactin.

Removal of the metabolites together with the biomass is strongly dependent of the pH values of the culture medium. Most metabolites are associated together with the biomass at low pH (pH 5.0). The metabolite is free off from the biomass when increasing the pH up to the measured pH 8.7—thus metabolite concentrations increase in the supernatant with increasing 10 pH. Iturin seems to be the most pH sensitive of the 3 investigated lipopeptides. At pH 8.7 only 60% of the offered Iturin is associated together with the spores. The remaining can be found in the supernatant.

The results also reveal that the presence of a geo/bio minerals—here classified as diatomic earth, volcanic rock, kaolin or silica—in the culture medium are necessary in order to capture the lipopeptides for pH values ≥5. All the tested minerals are capable to further reduce the amount of lipopeptides in the supernatant compare to the reference. It is evident that 95% of the available Fengycin, Iturin and Surfactin have been removed from in the culture medium after adding the tested geo/bio minerals. Adsorption properties of tested bio and geo minerals also reveal that the lipopeptides Fengycin, Iturin and Surfactin have different affinity to the tested minerals. For majority of the tested minerals adsorption profile of the lipopeptides are constant and thus independent of pH—e.g. Hyflo Supercel and Celite 545. For a few of the tested geo/bio minerals e.g. Harbolite 635 and Filtercel we still see a higher percentage removal of the lipopeptides in the culture medium (compare to the reference) but the removal of the lipopeptides in the culture medium decreased slightly with increasing pH in the pH range from pH 5.0 to pH 8.7.

Example 7. Adsorption of Fengycin, Iturin and Surfactin to Solid Support of Geopolymer Origin-Harvesting Active Metabolites of *Bacillus* Strains Using Different Loading Degree of Hyflo Supercel The *B. subtilis* culture medium (50 L) obtained according to Example 1, was after end fermentation divided in 5 fractions of 10 L's. 4 fractions were adjusted to pH 5.0 and the last fraction was maintained at pH 7.5.

The pH 7.5 fraction was incubated at room temperature for 2 hrs. @ 25 rpm. After end of incubation, biomass suspensions were isolated by centrifugation. Samples for lipopeptides analysis were taken from the culture medium before and after incubation. % recovered lipopeptides in the biomass suspensions were compare with the lipopeptides available in the start material.

For the remaining 4 pH adjusted fractions 0 kg, 0.2 kg, 0.4 kg and 0.6 kg of HyfloSupercel corresponding to a loading degree from 0-0.06 g Hyflo Supercel per ml spent culture medium were added to each of 10 L culture medium. The medium with the different amount of Hyflo Supercel were incubated at room temperature for 2 hrs. @ 25 rpm. After end of incubation, Hyflo Supercel/biomass suspensions were isolated by centrifugation. Samples for lipopeptides analysis were taken from, pH adjusted culture medium before incubation and the Hyflo Supercel/biomass suspensions isolated using centrifugation. % recovered lipopeptides in the Hyflo Supercel/biomass suspensions were compare with the lipopeptides available in the start material. Sample handling and lipopeptide analysis were as described in example 6.

The pH adjusted culture medium use as starting material for the loading experiments consisted of lipopeptides with a concentration on approx. 343 µg/ml for Fengycin, 311 µg/ml Iturin and 1245 µg/ml Surfactin.

Figure 1:
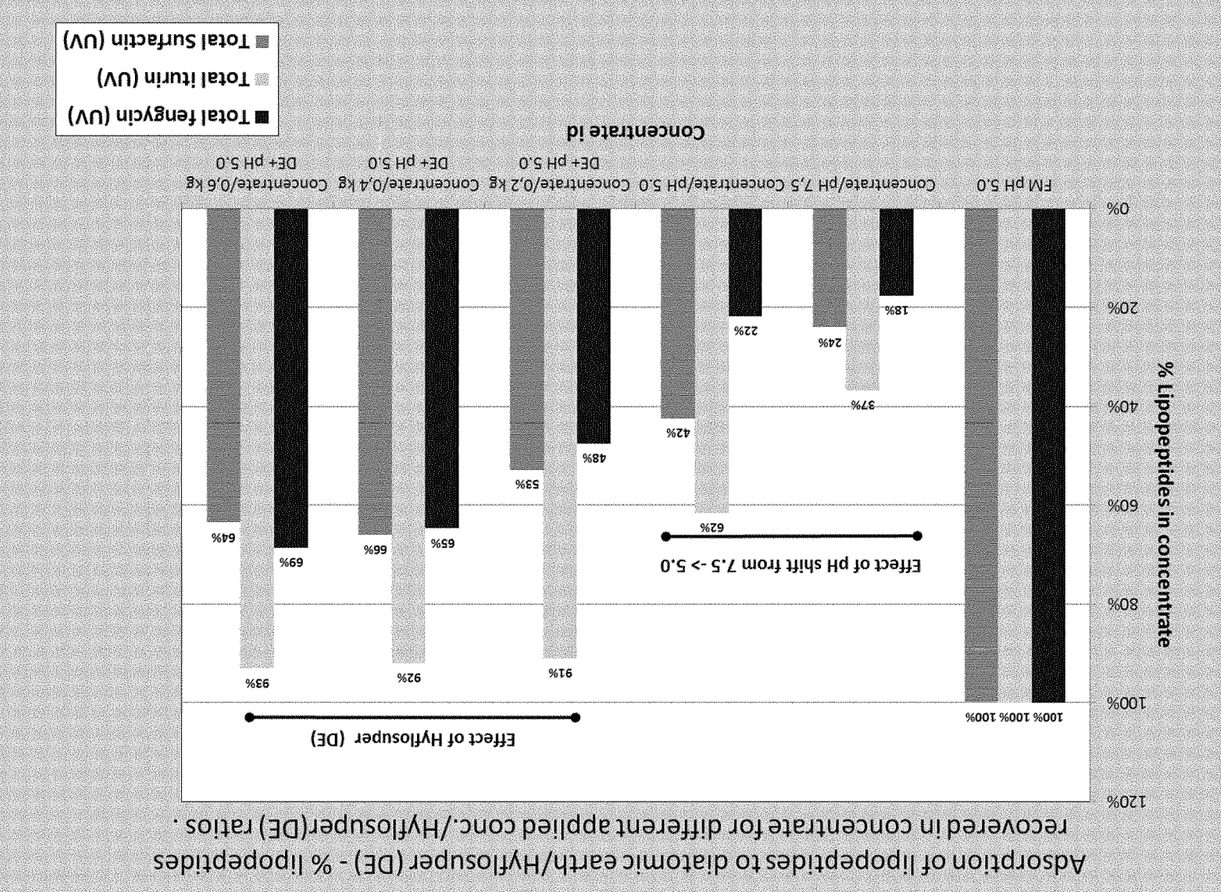
FIG. 1 depicts the recovery of fengycin, iturin and surfactin at different pH and different loading degrees of diatomic earth (Hyflo Supercel).

From FIG. 1 (depicting the Recovery of Fengycin, Iturin and Surfactin with different loading degrees of Hyflo Supercel) it follows that pH adjustment from pH 7.5 to pH 5.0 has a significant effect on removal of the lipopeptides in the culture medium. The recovery results in FIG. 1 also suggest that the presence of Hyflo Supercel in the culture medium is necessary in order to capture remaining lipopeptides in the culture medium.

Max recovery of the lipopeptides (65% Fengycin, 92% Iturin and 66% Surfactin) seems to level off with a loading degree of minimum on 0.04 g Hyflo Supercel/ml culture medium.

Example 8. Harvesting High Active Biomass from *Bacillus* Strain Reducing pH of the Culture Medium 4 L *B. subtilis* culture medium obtained according to Example 1 was after end fermentation divided in 4 fractions of 1 L's. The 4 fractions were adjusted to pH 4.5, 5.0, 6.0 and 7.5, respectively.

The pH adjusted culture medium use as starting material for the batch adsorption experiments consisted of lipopeptides with a concentration on approx. 200 µg/ml for Fengycin, 150 µg/ml Iturin and 400 µg/ml Surfactin.

For each of the pH adjusted fractions—0.5 ml culture medium was transferred to an Eppendorf test tube and incubated at room temperature for 2 hrs. @ 35 rpm on a blood mixer. Triplicate samples were prepared for each examined pH value.

After end of incubation, biomass concentrates (pellet) were isolated by centrifugation for 10 minutes. Supernatant was removed and transferred to a new Eppendorf test tube % distribution of lipopeptides in the supernatants and isolated pellet, respectively were µmeasure by taking samples from the isolated pellets and supernatants. Results for percentage distribution of Fengycin, Iturin and Surfactin are summarized in table 3 which gives the actual measured concentrations (µg/ml) for the lipopeptides in the supernatant and the pellet.

TABLE 3

| | 2 hrs | | | | Total | pH | 7.5 |
|---|---|---|---|---|---|---|---|
| Name | Average Pellet | % STDEV | Average Supernatant | % STDEV | conc. (µg/ml) | % bound to Pellet | % bound to Supernatant |
| Total fengycin UV (µg/mL) | 85 | 1% | 123 | 6% | 208 | 40.9% | 59.1% |
| Total iturin UV (µg/mL) | 110 | 12% | 26 | 1% | 136 | 80.6% | 19.4% |
| Total surfactin UV (µg/mL) | 297 | 7% | 70 | 3% | 367 | 80.8% | 19.2% |

| | 2 hrs | | | | Total | pH | 6.0 |
|---|---|---|---|---|---|---|---|
| Name | Average Pellet | % STDEV | Average Supernatant | % STDEV | conc. (µg/ml) | % bound to Pellet | % bound to Supernatant |
| Total fengycin UV (µg/mL) | 171 | 9% | 33 | 1% | 203 | 83.9% | 16.1% |
| Total iturin UV (µg/mL) | 137 | 12% | 17 | 1% | 154 | 89.0% | 11.0% |
| Total surfactin UV (µg/mL) | 369 | 11% | 25 | 0% | 395 | 93.6% | 6.4% |

TABLE 3-continued

| | 2 hrs | | | | Total conc. (μg/ml) | pH | 5.0 |
|---|---|---|---|---|---|---|---|
| Name | Average Pellet | % STDEV | Average Supernatant | % STDEV | | % bound to Pellet | % bound to Supernatant |
| Total fengycin UV (μg/mL) | 210 | 5% | 5 | 3% | 215 | 97.6% | 2.4% |
| Total iturin UV (μg/mL) | 130 | 18% | 12 | 0% | 142 | 91.6% | 8.4% |
| Total surfactin UV (μg/mL) | 401 | 8% | 1 | 0% | 402 | 99.8% | 0.2% |

| | 2 hrs | | | | Total conc. (μg/ml) | pH | 4.5 |
|---|---|---|---|---|---|---|---|
| Name | Average Pellet | % STDEV | Average Supernatant | % STDEV | | % bound to Pellet | % bound to Supernatant |
| Total fengycin UV (μg/mL) | 227 | 6% | 3 | 1% | 229 | 98.7% | 1.3% |
| Total iturin UV (μg/mL) | 151 | 8% | 12 | 0% | 163 | 92.5% | 7.5% |
| Total surfactin UV (μg/mL) | 407 | 13% | 1 | 0% | 408 | 99.8% | 0.2% |

It is evident that reducing the pH from pH 7.5 to pH 4.5 has a significant effect on removal of the lipopeptides in the culture medium. The lipopeptides follow the isolated pellets with decreasing pH values. The effect seems to level off when the pH value of the culture medium gets below pH 5. Below pH 5 all lipopeptides concentrations reach constant values in both the supernatant (close to zero) and the pellet (close to 100%). The calculated total concentration of the Fengycin, Iturin and Surfactin are as expected more or less constant.

Example 9. Harvesting High Active Biomass from *Bacillus* Strain Reducing pH of the Culture Medium Combined with the Use of a Flocculant 3 L *B. subtilis* culture medium obtained according to Example 1, was after end fermentation divided in 3 fractions of 1 L's. The 3 fractions were adjusted to pH 4.5, 5.0 and 7.5, respectively.

Each pH adjusted fraction was divided in 4 samples of 250 ml. 5 M stock solution of $CaCl_2$ was used to adjust the samples to 0 M, 50 mM, 100 mM and 200 mM $CaCl_2$, respectively. Each of the $CaCl_2$ adjusted fractions were incubated at room temperature for 1 hr @ 35 rpm on a blood mixer. 0.5 ml solution was transferred to an Eppendorf test tube and biomass concentrates (pellet) were isolated by centrifugation for 10 minutes. Concentration of Fengycin, Iturin and Surfactin were measure by taking samples from the isolated pellets and supernatants. The below tables give the actual measured concentrations (μg/ml) for the lipopeptides in the supernatant (table 5) and the pellet (table 4) for the different tested $CaCl_2$ concentrations and pH values.

TABLE 4

| Pellets: | | | | | |
|---|---|---|---|---|---|
| Conc. (mM) $CaCl_2$ flocculation pH 7.5 | 0 | | Sample id 2515 $CaCl_2$ | | |
| Lipo concentration | Pellet μg/ml | SD | Pellet μg/mlg | μg/ml | SD |
| Total fengycin (UV) μg/g | 471 | 11 | Total fengycin (MS) μg/g | 317 | 4 |
| Total iturin (UV) μg/g | 490 | 5 | Total iturin (MS) μg/g | 613 | 6 |
| Total Surfactin (UV) μg/g | 4285 | 49 | Total Surfactin (MS) μg/g | — | — |
| Conc. (mM) $CaCl_2$ flocculation pH 7.5 | 50 | | Sample id 2517 $CaCl_2$ | | |
| Lipo concentration | Pellet μg/ml | SD | Pellet μg/mlg | μg/ml | SD |
| Total fengycin (UV) μg/g | 1567 | 39 | Total fengycin (MS) μg/g | 925 | 25 |
| Total iturin (UV) μg/g | 2411 | 50 | Total iturin (MS) μg/g | 3387 | 54 |
| Total Surfactin (UV) μg/g | 7816 | 183 | Total Surfactin (MS) μg/g | — | — |
| Conc. (mM) $CaCl_2$ flocculation pH 7.5 | 100 | | Sample id 2519 $CaCl_2$ | | |
| Lipo concentration | Pellet μg/ml | SD | Pellet μg/mlg | μg/ml | SD |
| Total fengycin (UV) μg/g | 1711 | 54 | Total fengycin (MS) μg/g | 1158 | 34 |
| Total iturin (UV) μg/g | 2519 | 77 | Total iturin (MS) μg/g | 3516 | 46 |
| Total Surfactin (UV) μg/g | 7985 | 242 | Total Surfactin (MS) μg/g | — | — |

TABLE 4-continued

Pellets:

| | | | | | |
|---|---|---|---|---|---|
| Conc. (mM) CaCl₂ flocculation pH 7.5 | 200 | | Sample id 2521 CaCl₂ | | |
| Lipo concentration | Pellet µg/ml | SD | Pellet µg/mlg | µg/ml | SD |
| Total fengycin (UV) µg/g | 1863 | 114 | Total fengycin (MS) µg/g | 1595 | 30 |
| Total iturin (UV) µg/g | 2455 | 29 | Total iturin (MS) µg/g | 3398 | 39 |
| Total Surfactin (UV) µg/g | 8463 | 92 | Total Surfactin (MS) µg/g | — | — |
| Conc. (mM) CaCl₂ flocculation pH 5.0 | 0 | | Sample id 2523 CaCl₂ | | |
| Lipo concentration | Pellet µg/ml | SD | Pellet µg/mlg | µg/ml | SD |
| Total fengycin (UV) µg/g | 1997 | 24 | Total fengycin (MS) µg/g | 1560 | 15 |
| Total iturin (UV) µg/g | 2068 | 17 | Total iturin (MS) µg/g | 2862 | 17 |
| Total Surfactin (UV) µg/g | 8291 | 59 | Total Surfactin (MS) µg/g | — | — |
| Conc. (mM) CaCl₂ flocculation pH 5.0 | 50 | | Sample id 2525 CaCl₂ | | |
| Lipo concentration | Pellet µg/ml | SD | Pellet µg/mlg | µg/ml | SD |
| Total fengycin (UV) µg/g | 2623 | 32 | Total fengycin (MS) µg/g | 2162 | 28 |
| Total iturin (UV) µg/g | 2530 | 20 | Total iturin (MS) µg/g | 3324 | 36 |
| Total Surfactin (UV) µg/g | 9990 | 69 | Total Surfactin (MS) µg/g | — | — |
| Conc. (mM) CaCl₂ flocculation pH 5.0 | 100 | | Sample id 2527 CaCl₂ | | |
| Lipo concentration | Pellet µg/ml | SD | Pellet µg/mlg | µg/ml | SD |
| Total fengycin (UV) µg/g | 2702 | 51 | Total fengycin (MS) µg/g | 2263 | 15 |
| Total iturin (UV) µg/g | 2655 | 18 | Total iturin (MS) µg/g | 3419 | 11 |
| Total Surfactin (UV) µg/g | 11092 | 84 | Total Surfactin (MS) µg/g | — | — |
| Conc. (mM) CaCl₂ flocculation pH 5.0 | 200 | | Sample id 2529 CaCl₂ | | |
| Lipo concentration | Pellet µg/ml | SD | Pellet µg/mlg | µg/ml | SD |
| Total fengycin (UV) µg/g | 2743 | 73 | Total fengycin (MS) µg/g | 2342 | 52 |
| Total iturin (UV) µg/g | 2627 | 34 | Total iturin (MS) µg/g | 3446 | 54 |
| Total Surfactin (UV) µg/g | 10560 | 150 | Total Surfactin (MS) µg/g | — | — |
| Conc. (mM) CaCl₂ flocculation pH 4.5 | 0 | | Sample id 2531 CaCl₂ | | |
| Lipo concentration | Pellet µg/ml | SD | Pellet µg/mlg | µg/ml | SD |
| Total fengycin (UV) µg/g | n/a | | Total fengycin (MS) µg/g | 2089 | 39 |
| Total iturin (UV) µg/g | n/a | | Total iturin (MS) µg/g | 2226 | 29 |
| Total Surfactin (UV) µg/g | 8482 | 137 | Total Surfactin (MS) µg/g | — | — |
| Conc. (mM) CaCl₂ flocculation pH 4.5 | 50 | | Sample id 2533 CaCl₂ | | |
| Lipo concentration | Pellet µg/ml | SD | Pellet µg/mlg | µg/ml | SD |
| Total fengycin (UV) µg/g | n/a | | Total fengycin (MS) µg/g | 2974 | 30 |
| Total iturin (UV) µg/g | n/a | | Total iturin (MS) µg/g | 3090 | 17 |
| Total Surfactin (UV) µg/g | 10896 | 138 | Total Surfactin (MS) µg/g | — | — |
| Conc. (mM) CaCl₂ flocculation pH 4.5 | 100 | | Sample id 2535 CaCl₂ | | |
| Lipo concentration | Pellet µg/ml | SD | Pellet µg/mlg | µg/ml | SD |
| Total fengycin (UV) µg/g | n/a | | Total fengycin (MS) µg/g | 923 | 2 |
| Total iturin (UV) µg/g | n/a | | Total iturin (MS) µg/g | 590 | 2 |
| Total Surfactin (UV) µg/g | n/a | | Total Surfactin (MS) µg/g | — | — |
| Conc. (mM) CaCl₂ flocculation pH 4.5 | 200 | | Sample id 2537 CaCl₂ | | |

TABLE 4-continued

| Pellets: | | | | | |
|---|---|---|---|---|---|
| Lipo concentration | Pellet μg/ml | SD | Pellet μg/mlg | μg/ml | SD |
| Total fengycin (UV) μg/g | n/a | | Total fengycin (MS) μg/g | 928 | 2 |
| Total iturin (UV) μg/g | n/a | | Total iturin (MS) μg/g | 566 | 2 |
| Total Surfactin (UV) μg/g | n/a | | Total Surfactin (MS) μg/g | — | — |

TABLE 5

| Supernatant: | | | | | |
|---|---|---|---|---|---|
| Conc. (mM) CaCl2 flocculation pH 7.5 | 0 | | Sample id 2514 CaCl2 | | |
| Lipo concentration | Supernatant μg/ml | SD | Supernatant μg/ml | μg/ml | SD |
| Total fengycin (UV) μg/g | 310 | 8 | Total fengycin (MS) μg/g | 251 | 2 |
| Total iturin (UV) μg/g | 369 | 4 | Total iturin (MS) μg/g | 361 | 3 |
| Total Surfactin (UV) μg/g | 791 | 27 | Total Surfactin (MS) μg/g | — | — |
| Conc. (mM) CaCl2 flocculation pH 7.5 | 50 | | Sample id 2516 CaCl2 | | |
| Lipo concentration | Supernatant μg/ml | SD | Supernatant μg/ml | μg/ml | SD |
| Total fengycin (UV) μg/g | 194 | 4 | Total fengycin (MS) μg/g | 150 | 1 |
| Total iturin (UV) μg/g | 113 | 3 | Total iturin (MS) μg/g | 89 | 0 |
| Total Surfactin (UV) μg/g | 236 | 1 | Total Surfactin (MS) μg/g | — | — |
| Conc. (mM) CaCl2 flocculation pH 7.5 | 100 | | Sample id 2518 CaCl2 | | |
| Lipo concentration | Supernatant μg/ml | SD | Supernatant μg/ml | μg/ml | SD |
| Total fengycin (UV) μg/g | 139 | 3 | Total fengycin (MS) μg/g | 109 | 0 |
| Total iturin (UV) μg/g | 87 | 2 | Total iturin (MS) μg/g | 45 | 1 |
| Total Surfactin (UV) μg/g | 149 | 2 | Total Surfactin (MS) μg/g | — | — |
| Conc. (mM) CaCl2 flocculation pH 7.5 | 200 | | Sample id 2520 CaCl2 | | |
| Lipo concentration | Supernatant μg/ml | SD | Supernatant μg/ml | μg/ml | SD |
| Total fengycin (UV) μg/g | 66 | 2 | Total fengycin (MS) μg/g | 42 | 1 |
| Total iturin (UV) μg/g | 81 | 4 | Total iturin (MS) μg/g | 35 | 1 |
| Total Surfactin (UV) μg/g | 79 | 5 | Total Surfactin (MS) μg/g | — | — |
| Conc. (mM) CaCl2 flocculation pH 5.0 | 0 | | Sample id 2522 CaCl2 | | |
| Lipo concentration | Supernatant μg/ml | SD | Supernatant μg/ml | μg/ml | SD |
| Total fengycin (UV) μg/g | 75 | 4 | Total fengycin (MS) μg/g | 46 | 0 |
| Total iturin (UV) μg/g | 130 | 7 | Total iturin (MS) μg/g | 131 | 0 |
| Total Surfactin (UV) μg/g | 75 | 0 | Total Surfactin (MS) μg/g | — | — |
| Conc. (mM) CaCl2 flocculation pH 5.0 | 50 | | Sample id 2524 CaCl2 | | |
| Lipo concentration | Supernatant μg/ml | SD | Supernatant μg/ml | μg/ml | SD |
| Total fengycin (UV) μg/g | 7 | 1 | Total fengycin (MS) μg/g | 3 | 0 |
| Total iturin (UV) μg/g | 61 | 1 | Total iturin (MS) μg/g | 17 | 0 |
| Total Surfactin (UV) μg/g | 12 | 1 | Total Surfactin (MS) μg/g | — | — |
| Conc. (mM) CaCl2 flocculation pH 5.0 | 100 | | Sample id 2526 CaCl2 | | |

TABLE 5-continued

| Supernatant: | | | | | |
|---|---|---|---|---|---|
| Lipo concentration | Supernatant µg/ml | SD | Supernatant µg/ml | µg/ml | SD |
| Total fengycin (UV) µg/g | 3 | 1 | Total fengycin (MS) µg/g | 2 | 0 |
| Total iturin (UV) µg/g | 56 | 1 | Total iturin (MS) µg/g | 15 | 0 |
| Total Surfactin (UV) µg/g | 12 | 1 | Total Surfactin (MS) µg/g | — | — |

| Conc. (mM) CaCl2 flocculation pH 5.0 | 200 | | Sample id 2528 CaCl2 | | |
|---|---|---|---|---|---|
| Lipo concentration | Supernatant µg/ml | SD | Supernatant µg/ml | µg/ml | SD |
| Total fengycin (UV) µg/g | 4 | 1 | Total fengycin (MS) µg/g | 2 | 0 |
| Total iturin (UV) µg/g | 52 | 0 | Total iturin (MS) µg/g | 16 | 0 |
| Total Surfactin (UV) µg/g | 15 | 0 | Total Surfactin (MS) µg/g | — | — |

| Conc. (mM) CaCl2 flocculation pH 4.5 | 0 | | Sample id 2530 CaCl2 | | |
|---|---|---|---|---|---|
| Lipo concentration | Supernatant µg/ml | SD | Supernatant µg/ml | µg/ml | SD |
| Total fengycin (UV) µg/g | 46 | 7 | Total fengycin (MS) µg/g | 29 | 0 |
| Total iturin (UV) µg/g | 121 | 2 | Total iturin (MS) µg/g | 210 | 1 |
| Total Surfactin (UV) µg/g | 61 | 2 | Total Surfactin (MS) µg/g | — | — |

| Conc. (mM) CaCl2 flocculation pH 4.5 | 50 | | Sample id 2532 CaCl2 | | |
|---|---|---|---|---|---|
| Lipo concentration | Supernatant µg/ml | SD | Supernatant µg/ml | µg/ml | SD |
| Total fengycin (UV) µg/g | 13 | 2 | Total fengycin (MS) µg/g | 6 | 0 |
| Total iturin (UV) µg/g | 78 | 1 | Total iturin (MS) µg/g | 66 | 0 |
| Total Surfactin (UV) µg/g | 24 | 1 | Total Surfactin (MS) µg/g | — | — |

| Conc. (mM) CaCl2 flocculation pH 4.5 | 100 | | Sample id 2534 CaCl2 | | |
|---|---|---|---|---|---|
| Lipo concentration | Supernatant µg/ml | SD | Supernatant µg/ml | µg/ml | SD |
| Total fengycin (UV) µg/g | 6 | 2 | Total fengycin (MS) µg/g | 4 | 0 |
| Total iturin (UV) µg/g | 61 | 1 | Total iturin (MS) µg/g | 45 | 0 |
| Total Surfactin (UV) µg/g | 17 | 1 | Total Surfactin (MS) µg/g | — | — |

| Conc. (mM) CaCl2 flocculation pH 4.5 | 200 | | Sample id 2536 CaCl2 | | |
|---|---|---|---|---|---|
| Lipo concentration | Supernatant µg/ml | SD | Supernatant µg/ml | µg/ml | SD |
| Total fengycin (UV) µg/g | 8 | 2 | Total fengycin (MS) µg/g | 4 | 0 |
| Total iturin (UV) µg/g | 57 | 0 | Total iturin (MS) µg/g | 41 | 0 |
| Total Surfactin (UV) µg/g | 18 | 0 | Total Surfactin (MS) µg/g | — | — |

Results from the test reveal that applied $CaCl_2$) conc. and pH of the *B. subtilis* culture medium both have an influence on the removal of lipopeptides Fengycin, Iturin and Surfactin. Reducing the pH itself from pH 7.5 to pH 4.5 ($CaCl_2$) conc. equal to 0 mM) has a positive effect on removal of the lipopeptides in the culture medium. The lipopeptides follow the isolated pellets with decreasing pH values. The effect seems to level off when the pH value of the culture medium reaches pH 5. Additional lipopeptides left back in the culture medium can subsequently be stripped off by increasing the $CaCl_2$) concentration in the culture medium. It is evident that the lipopeptides are isolated together with the biomass with increasing $CaCl_2$) concentration and that the lipopeptide concentration in the supernatant at the same time is reduced.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

[1] M. Shoda: Bacterial Control of Plant Disease, Journal of Bioscience and Bioengineering, pp. 515-521, 200.
[2] H. P. Bais, R. Fall and J. M. Vivanco: Biocontrol of *Bacillus subtilis* against infection of *Arabidopsis* roots by *Pseudomonas syringae* is facilitated by biofilm formation and surfactin production, Plant Physiology, vol. 134, pp. 307-319, 2004.
[3] T. Stein: *Bacillus subtilis* antibiotics: structures, syntheses and specific functions, Molecular Microbiology, vol. 56, pp. 854-857, 2005.
[4] M. Ongena and P. Jacques: *Bacillus* lipopeptides: versatile weapons for plant disease biocontrol, Applied Microbiology and Biotechnology, vol. 16, No. 3, pp. 115-125, 2008.
[5] US 20150147303
[6] WO14178032A
[7] D V Petrovic et al: On the particles size distributions of Diatomaceous earth and perlite granulations, J Mechanical Engineering 57, 843-50, 2011
[8] CN103478146A, adsorption on macroporous resin
[9] WO15024672A1
[10] U.S. Pat. No. 5,470,827

All references cited in this patent document are hereby incorporated herein in their entirety by reference.

The invention claimed is:

1. A process for harvesting a biomass comprising bacterial cells and/or spores and exhibiting fungicidal activity, comprising:
  (a) propagating a lipoprotein-producing and/or glycolipid-producing bacterial strain in a growth medium to obtain a culture medium;
  (b) ensuring the pH of the culture medium is in a range from 2.5 to 5.5;
  (c) optionally, before, during, or after step (b), adding a geopolymer to the culture medium;
  (d) separating the biomass from the culture medium having a pH in a range from 2.5 to 5.5;
  (e) optionally, adding an excipient to the biomass, and, optionally, adjusting the pH of the biomass to be in a range from 5.5 to 8.0; and
  (f) optionally, drying the biomass.

2. The process of claim 1, wherein in step (a) the propagating is carried out at a pH above 5.7.

3. The process of claim 1, wherein step (b) comprises ensuring the pH of the culture medium is in a range from 3.0 to 5.0, and wherein step (d) comprises separating the biomass from the culture medium having a pH in a range from 3.0 to 5.0.

4. The process of claim 1, wherein step (d) comprises separating the biomass from the culture medium by a process selected from centrifugation and filtration.

5. The process of claim 1, wherein step (f) comprises drying the biomass by a process selected from spray drying, freeze drying, and vacuum drying.

6. The process of claim 1, wherein in step (b) the pH of the culture medium is maintained in a range from 2.5 to 5.5 for a period of time of at least 10 minutes.

7. The process of claim 1, wherein a geopolymer is added and is selected from diatomite, kieselguhr, kaolin, chinese clay, bentonite, talcum, volcanic ash, volcanic rock, clay, lignin, drilling mud, diatomaceous earth, synthetic silica, surface-treated diatomaceous earth, and metal silicate.

8. The process of claim 7, wherein the geopolymer is selected from diatomaceous earth and surface-treated diatomaceous earth.

9. The process of claim 1, wherein the geopolymer is added in an amount of from 0.02 g to 0.3 g/ml of the culture medium.

10. The process of claim 1, wherein the bacterial strain is of a *Bacillus* species.

11. The process of claim 1, wherein the bacterial strain produces a lipoprotein and/or glycolipid selected from surfactin, iturin, plipastatin, arthrofactin, serrawettin, fengycin, and derivatives thereof.

12. The process of claim 1, wherein the method further comprises, prior to step (d), adding a flocculent to the culture medium.

13. The process of the claim 12, wherein the pH is maintained in a range of 4.5 to 7.5 during flocculation.

* * * * *